(12) United States Patent
Beebe et al.

(10) Patent No.: US 7,766,902 B2
(45) Date of Patent: Aug. 3, 2010

(54) MICROFLUIDIC DEVICE FOR DRUG DELIVERY

(75) Inventors: David J. Beebe, Monona, WI (US); Michael J. MacDonald, Madison, WI (US); David T. Eddington, Madison, WI (US); Glennys A. Mensing, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 288 days.

(21) Appl. No.: 10/762,664

(22) Filed: Jan. 22, 2004

(65) Prior Publication Data

US 2005/0038379 A1 Feb. 17, 2005

Related U.S. Application Data

(63) Continuation of application No. 10/640,345, filed on Aug. 13, 2003, now abandoned.

(51) Int. Cl.
*A61K 9/22* (2006.01)
*A61M 31/00* (2006.01)

(52) U.S. Cl. ...................... 604/890.1; 604/65

(58) Field of Classification Search ............ 604/65–67, 604/890.1, 131–133, 151, 153
See application file for complete search history.

(56) References Cited

U.S. PATENT DOCUMENTS

| | | | |
|---|---|---|---|
| 4,552,561 A * | 11/1985 | Eckenhoff et al. ....... | 604/891.1 |
| 4,556,086 A * | 12/1985 | Raines ....................... | 137/852 |
| 5,109,850 A * | 5/1992 | Blanco et al. ............... | 600/368 |
| 5,224,843 A * | 7/1993 | van Lintel ................. | 417/413.2 |
| 5,466,261 A * | 11/1995 | Richelsoph ............... | 623/23.47 |
| 5,693,018 A * | 12/1997 | Kriesel et al. ............... | 604/132 |
| 5,716,343 A * | 2/1998 | Kriesel et al. ............... | 604/132 |
| 5,848,991 A * | 12/1998 | Gross et al. ................. | 604/140 |
| 5,935,593 A | 8/1999 | Ron et al. | |
| 6,268,161 B1 | 7/2001 | Han et al. ..................... | 435/14 |
| 6,416,495 B1 * | 7/2002 | Kriesel et al. ............... | 604/132 |
| 6,475,750 B1 | 11/2002 | Han et al. ..................... | 435/14 |
| 6,485,461 B1 | 11/2002 | Mason et al. ................ | 604/132 |
| 6,514,689 B2 | 2/2003 | Han et al. ....................... | 435/4 |
| 6,523,559 B2 * | 2/2003 | Beebe et al. ..................... | 137/3 |
| 6,689,100 B2 * | 2/2004 | Connelly et al. ............ | 604/117 |
| 7,047,915 B2 | 7/2006 | Soreq et al. | |
| 2002/0063060 A1 | 5/2002 | Gascoyne et al. ........... | 204/471 |
| 2002/0117517 A1 | 8/2002 | Unger et al. ................. | 222/214 |
| 2002/0193729 A1 | 12/2002 | Cormier et al. ............... | 604/46 |
| 2003/0196900 A1 * | 10/2003 | Chuang et al. ............... | 204/600 |
| 2004/0068224 A1 * | 4/2004 | Couvillon et al. ............. | 604/67 |
| 2004/0248326 A1 * | 12/2004 | Ziaie et al. ........................ | 438/1 |
| 2006/0002804 A1 * | 1/2006 | Jiang et al. ............... | 417/410.1 |

* cited by examiner

*Primary Examiner*—Kevin C Sirmons
*Assistant Examiner*—Andrew M Gilbert
(74) *Attorney, Agent, or Firm*—Boyle Fredrickson, S.C.

(57) ABSTRACT

A microfluidic device is provided for delivering a drug to an individual. The microfluidic device includes a body that defines a reservoir for receiving the drug therein. A valve interconnects the reservoir to an output needle that is insertable into the skin of an individual. A pressure source urges the drug from the reservoir toward the needle. The valve is movable between a closed position preventing the flow of the drug from the reservoir to the output needle and an open position allowing for the flow of the drug from the reservoir to the output needle in response to a predetermined condition in the physiological fluids of the individual.

2 Claims, 4 Drawing Sheets

MICROFLUIDIC DEVICE FOR DRUG DELIVERY

CROSS REFERENCE TO RELATED APPLICATION

This application is a continuation application of present U.S. application Ser. No. 10/640,345, filed Aug. 13, 2003, (now abandoned) and entitled "Microfluidic Device For Drug Delivery," the entirety of which is incorporated herein by reference.

REFERENCE TO GOVERNMENT GRANT

This invention was made with United States government support awarded by the following agencies: NASA NAG8-1672. The United States has certain rights in this invention.

FIELD OF THE INVENTION

This invention relates generally to microfluidic devices, and in particular, to a microfluidic device for delivering a steady infusion of a drug to an individual.

BACKGROUND AND SUMMARY OF THE INVENTION

As is known, the pharmaceutical industry has had limited success overcoming the challenges of delivering pharmaceuticals to patients. The oral ingestion of pharmaceuticals is considered the safest, most convenient and most economical method of drug administration. As compared to present alternatives, patient acceptance and adherence to a dosing regimen is typically higher among orally delivered pharmaceuticals. However, the oral delivery of many pharmaceuticals is not possible because the pharmaceuticals are either too large or too electrically charged to pass through the small intestine to reach the bloodstream. In addition, many pharmaceuticals that are unable to withstand the environment of the digestive tract or to penetrate the dermis need to be injected into the patient (e.g. insulin, proteins). As hereinafter described, the injection of pharmaceuticals into a patient has certain drawbacks.

By way of example, insulin is often used to treat diabetes, a disorder of metabolism. Most of the foods eaten by individuals are broken down in the body into glucose, the form of sugar in the blood. Glucose is the main source of fuel for the body. After digestion, the glucose passes into the bloodstream where it is used by the cells for growth and energy. For glucose to get into cells, insulin must be present. Insulin is a hormone that is automatically produced by a healthy pancreas to move glucose from blood into our cells. In people with diabetes, however, the pancreas either produces little or no insulin, or the cells do not respond appropriately to the insulin that is produced. As a result, glucose builds up in the blood, overflows into the urine, and passes out of the body. Consequently, the body loses its main source of fuel, even though the blood contains large amounts of glucose.

In order to use the glucose present in the body, a diabetic must take insulin injections every day. The amount of insulin taken by an individual must be balanced with the individual's food intake and daily activities. Consequently, blood glucose levels must be closely monitored through frequent blood glucose checking to insure that blood glucose levels do not fall too low or rise too high. When blood glucose levels drop too low from certain diabetes medicines—a condition known as hypoglycemia—a person can become nervous, shaky, and confused. If blood glucose falls, judgment can be impaired and a person could faint. Alternatively, a person can also become ill if blood glucose levels rise too high, a condition known as hyperglycemia. Although daily insulin injections are a great inconvenience, they are necessary for a diabetics' survival.

Most people with diabetes administer their own insulin after learning the proper techniques for insulin preparation and injection. The goal of insulin administration is to give enough insulin to cover the amount of food (especially carbohydrates) that a person consumes so that blood glucose levels remain normal throughout the day and night. It can be appreciated that various factors such as the type of insulin used, the size of the person, the amount, type, and time that meals are eaten, and the activity and exercise patterns of the person effect the amount of insulin that is required by an individual. It takes a dedicated patient to continually monitor their blood glucose level and administer the repeated multiple injections required. Therefore, an autonomous infusion system that provides a steady infusion of pharmaceuticals to an individual when needed would constitute a significant advancement in the art.

Therefore, it is a primary object and feature of the present invention to provide a microfluidic device that delivers a steady infusion of pharmaceuticals to an individual when needed.

It is a further object and feature of the present invention to provide a microfluidic device that delivers a steady infusion of pharmaceuticals to an individual under autonomous control.

It is a still further object and feature of the present invention to provide a microfluidic device for delivering a steady infusion of pharmaceuticals to an individual that is simple to utilize and inexpensive to manufacture.

In accordance with the present invention, a microfluidic device is provided for delivering a drug to an individual. The microfluidic device includes a reservoir for receiving a drug therein and an output needle. The output needle has an input in communication with the reservoir and an output receivable within the individual. A pressure source is engageable with the reservoir for urging the drug from the reservoir through the output needle.

The microfluidic device includes a flexible membrane isolating the pressure source from the reservoir. A valve operatively connects the input of the output needle and the reservoir. The valve defines a chamber having an input communicating with the reservoir and an output communicating with the input of the output needle. The valve also includes a flexible membrane dividing the chamber into a first drug flow portion and a second trigger receiving portion. A trigger is disposed in the trigger receiving portion in the chamber of the valve. The trigger has a first configuration preventing the flow of the drug through the chamber and a second configuration allowing for the flow of the drug through the chamber.

A first sensing needle has an input receivable in the individual and an output within the trigger receiving portion of the chamber. The first sensing needle allows physiological fluids to pass from the individual to the trigger receiving portion of the chamber. A second sensing needle may also be provided. The second sensing needle has an input receivable in the individual and an output within the trigger receiving portion of the chamber. The second sensing needle allows physiological fluids to pass from the individual to the trigger receiving portion of the chamber in the valve. It is contemplated for the trigger to include a hydrogel post that is expandable in response to exposure to a predetermined condition in the physiological fluid. Hydrogels are stimuli crosslinked polymeric materials that change their state of swelling, as manifested by a change in size, in response to chemical and physical changes in their surrounding environment. It is contemplated for the hydrogel post to be formed entirely from a hydrogel material or to be formed from a solid post having the hydrogel material formed thereabout.

The microfluidic device also may include a second reservoir for receiving a bolus of the drug therein. An actuation device is also provided. The actuation device is movable between a non-actuated position and an actuated position wherein the bolus of the drug is urged through the outlet needle and into the individual.

In accordance with a further aspect of the present invention, a microfluidic device is provided for delivering a drug to an individual. The microfluidic device includes a body that defines a reservoir for receiving the drug therein and a conduit. The conduit has an input communicating with the reservoir and an output. An output needle has an input receivable in the body to communicate with the output of the conduit and an output outside of the body for insertion into the individual. A pressure source is engageable with the reservoir for urging the drug from the reservoir through the output needle.

It is contemplated that the output needle be removable from the body. In addition, it is contemplated that a flexible membrane isolate the pressure source from the reservoir. The conduit may include a valve for controlling the flow of the drug from the reservoir to the output needle. The valve defines a valve chamber and is movable between a non-actuated position wherein the valve prevents the flow of the drug from the reservoir to the output needle and an actuated position wherein the valve allows for the flow of the drug from the reservoir to the output needle. A flexible membrane divides the valve chamber into a first drug flow portion and a second trigger receiving portion. A trigger is disposed in a trigger receiving portion of the valve chamber. The trigger has a first configuration with the valve in the non-actuated position and a second configuration with the valve in the actuated position. A first sensing needle has an input receivable in the individual and an output within the trigger receiving portion of the valve chamber. The first sensing needle allows physiological fluids to pass from the individual to the trigger receiving portion of the valve chamber. The trigger includes a hydrogel post. The hydrogel post changes the configuration in a response to exposure to a predetermined condition in the physiological fluids.

The body may also define a second reservoir for receiving a bolus of the drug therein. An actuation device is also provided. The actuation device moves between a non-actuated position and an actuated position wherein the bolus of the drug is urged from the second reservoir; through the outlet needle; and into the individual.

In accordance with a still further aspect of the present invention, a microfluidic device is provided for delivering a drug to an individual. The microfluidic device includes a body defining a reservoir for receiving the drug and an output needle. The output needle has an input in communication with the reservoir and an output receivable within the individual. An adhesive is provided for affixing the body to the individual.

The microfluidic device may also include a pressure source engageable with the reservoir for urging the drug from the reservoir through the output needle. A docketing station supports the output needle. The docketing station is removably connected to the body. A valve defining a chamber interconnects the reservoir and the output needle. The valve is movable between a non-actuated position wherein the valve prevents the flow of the drug from the reservoir to the output needle and an actuated position wherein the valve allows for the flow of the drug from the reservoir to the output needle. The valve includes a flexible membrane for dividing the valve chamber into a first drug flow portion and a second trigger receiving portion. A trigger is positioned within the trigger receiving portion of the valve chamber. The trigger has a first configuration with the valve in a non-actuated position and a second configuration with the valve in the actuated position. A first sensing needle has an input receivable in the individual and an output within the trigger receiving portion of the valve chamber. The first sensing needle allows physiological fluids to pass from the individual to the trigger receiving portion of the valve chamber. The trigger may include a hydrogel post that changes configuration in response to exposure to a predetermined condition in the physiological fluids.

The body may also define a second reservoir for receiving a bolus of the drug therein. An actuation device is also provided. The actuation device is movable between a non-actuated position and an actuated position wherein the bolus of the drug is urged from the second reservoir, through the outlet needle, and into the individual.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiments.

In the drawings.

DETAILED DESCRIPTION OF THE PREFERRED EMBODIMENT

Figure 1:
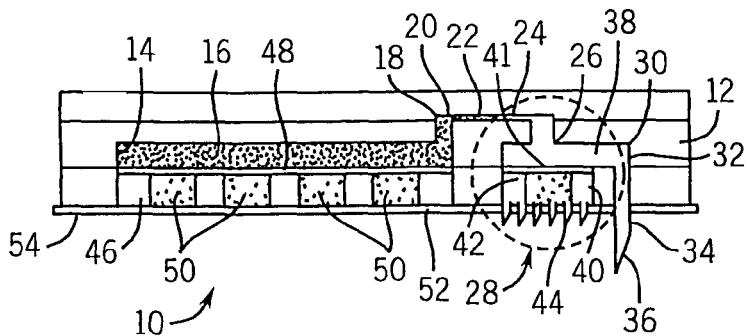
FIG. 1 is a schematic, cross-sectional view showing a first embodiment of a microfluidic device in accordance with the present invention.

Referring to FIGS. 1-4, a microfluidic device in accordance with the present invention is generally designated by the reference numeral 10. Microfluidic device 10 includes body 12 formed from polydimethylsiloxane (PDMS) or the like in any conventional manner such as by compression micro-molding or rapid prototyping. Body 12 defines reservoir 14 for the receiving and the storage of drug 16 therein. Reservoir 14 includes output 18 that communicates with input 20 of flow conduit 22. Output 24 of flow conduit 22 communicates with the input 26 of valve 28. Output 30 of valve 28 communicates with input 32 of outlet needle 34 that projects from body 12. Outlet needle 34 includes outlet end 36 that is injectable into an individual, as hereinafter described.

Valve 28 includes a valve chamber defined by drug flow portion 38 and trigger receiving portion 40. Drug flow portion 38 and trigger receiving portion 40 of the valve chamber within valve 28 are isolated from each other by flexible membrane 41. As is conventional, valve 28 is movable between a closed position, FIGS. 2-3, wherein drug 16 is prevented from flowing through drug flow portion 38 of valve 28 to outlet needle 34 and an open position, FIGS. 1 and 4, wherein drug 16 is free to flow through drug flow portion 38 of valve 16 to outlet needle 34.

Hydrogel trigger 42 is positioned within trigger receiving portion 40 of the valve chamber within valve 28. Hydrogels are stimuli crosslinked polymeric materials that change their state of swelling, as manifested by a change in size, in response to chemical and physical changes in their surrounding environment. In the present invention, hydrogel trigger 42 is sensitive to a predetermined condition within the physiological fluids received in trigger receiving chamber 40 of the valve chamber within valve 28. In the disclosed embodiment, hydrogel trigger 42 shrinks in response to exposure to the predetermined condition within the physiological fluids. However, it can be appreciated that hydrogel trigger 42 may expand in response to such condition if so desired.

The valve 28 further includes a plurality of sensing needles 44 extending between trigger receiving portion 40 of the valve chamber within valve 28 and the environment outside body 12. Sensing needles 44 may take the form of an array of micro-needles or a single needle similar to outlet needle 34. Sensing needles 44 allow physiological fluids to flow into trigger receiving portion 40 of the valve chamber within valve 28, for reasons hereinafter described.

Microfluidic device 10 further defines pressure source cavity 46 that is isolated from reservoir 14 by flexible membrane 48. A plurality of hydrogel pressure sources 50 are spatially disposed within pressure source cavity 46. Hydrogel pressure sources 50 are responsive to a trigger such as a buffer solution injectable into pressure source cavity 46 either during or after fabrication of body 12. In the depicted embodiment, the buffer solution injected into pressure source cavity 46 and body 12 causes hydrogel pressure sources 50 to expand and exert a pressure on flexible membrane 48, for reasons hereinafter described.

In operation, microfluidic device 10 is positioned adjacent the skin of an individual and urged therein such that input 36 of outlet needle 34 communicates with the subcutaneous layer of the skin of an individual. Sensing needles 44 are of sufficient depth within the skin of the individual such that physiological fluids may flow into trigger receiving portion 40 of the valve chamber within valve 28. Adhesive 52 is provided along the lower surface 54 of body 12 so as to affix microfluidic device 10 to the outer surface of the skin of the individual.

Figure 2:
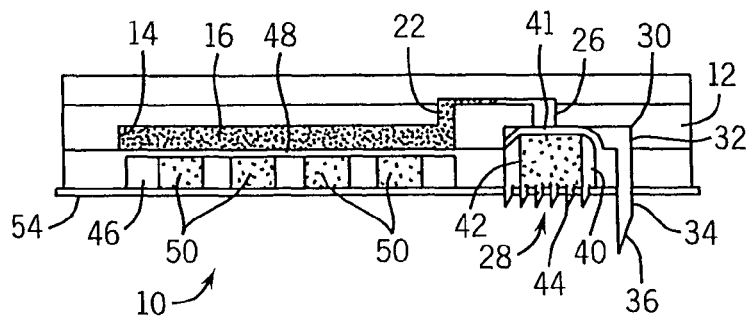
FIG. 2 is a schematic, cross-sectional view of the microfluidic device of FIG. 1 with the valve in a closed position.
Figure 3:
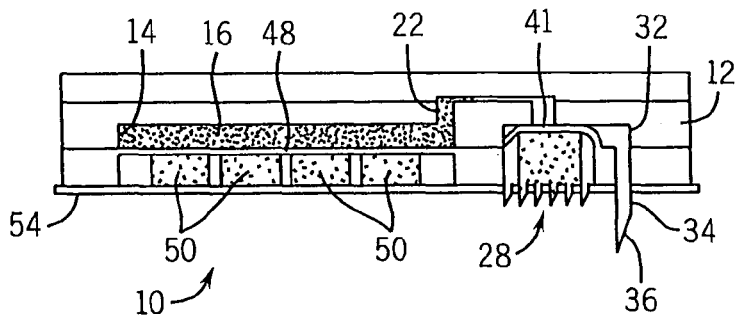
FIG. 3 is a schematic, cross-sectional view of the microfluidic device of FIG. 1 showing the triggering of the pressure source.
Figure 4:
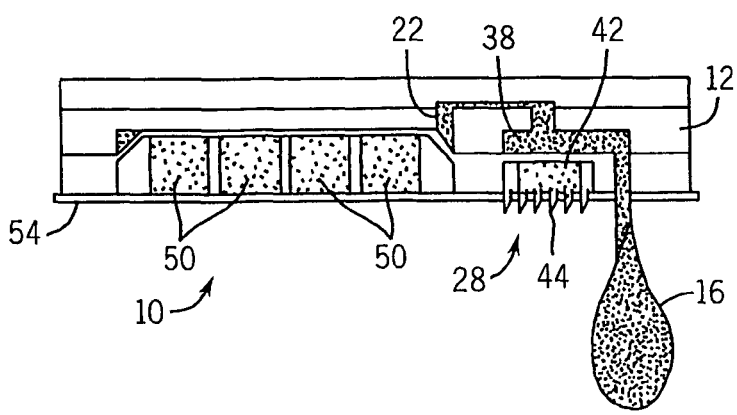
FIG. 4 is a schematic, cross-sectional view showing the microfluidic device of FIG. 1 with the valve in an open position.

In its initial configuration, FIGS. 2-3, hydrogel trigger 42 within trigger receiving portion 40 of the valve chamber of the valve 28 urges flexible membrane 41 over input 26 to drug flow portion 38 of the valve chamber within valve 28 so as to prevent drug 16 from flowing from reservoir 14 to outlet needle 34. In other words, valve 28 is in the closed position. Hydrogel pressure sources 50 are triggered so as to expand, FIG. 3, generating pressure on drug 16 within reservoir 14 in body 12. The pressure generated by hydrogel pressure sources 50 urges drug 16 into flow conduit 22 toward valve 28.

As heretofore described, hydrogel trigger 42 is responsive to a predetermined condition within the physiological fluid flowing into trigger receiving portion 40 of the valve chamber of valve 28 through sensing needles 44. By way of example, it is contemplated that hydrogel trigger 42 shrink in response to a predetermined concentration of glucose in the physiological fluid and that drug 16 within reservoir 14 be insulin. Upon the sensing of a predetermined concentration of glucose in the physiological fluid, hydrogel trigger 42 begins to shrink. As hydrogel trigger 42 within trigger receiving portion 40 of the valve chamber of valve 28 shrinks, flexible membrane 41 is withdrawn from input 26 of valve 28 so as to open valve 28. As a result, drug 16 is allowed to flow through drug flow portion 38 of the valve chamber of valve 28 into and through outlet needle 34, FIG. 4. With valve 28 in the open position, FIG. 4, hydrogel pressure sources 50 continue to expand thereby urging flexible membrane 48 into reservoir 14 so as to urge the drug 16 therefrom. As described, drug 16 flows from reservoir 14 through flow conduit 22; through drug flow portion 38 of the valve chamber in valve 28; through outlet needle 34; and into the individual.

In the event that the glucose level of the physiological fluid received within trigger receiving portion 40 of the valve chamber in valve 28 drops below a predetermined level, hydrogel trigger 42 will once again expand so as to urge flexible membrane 41 against input 26 to valve 28, thereby closing valve 28. As a result, the flow of drug 16 to the individual is stopped.

Figure 5:
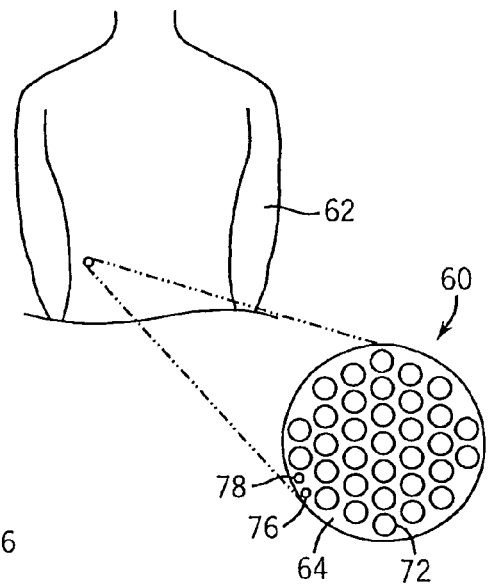
FIG. 5 is a top plan view showing an alternate embodiment of a microfluidic device in accordance with the present invention and a torso to which a microfluidic device may be affixed.
Figure 6:
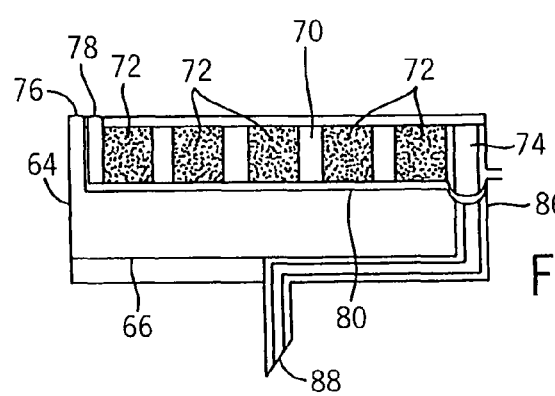
FIG. 6 is a schematic, cross-sectional view of the microfluidic device of FIG. 5 with the reservoir thereof empty.

Referring to FIG. 5, an alternate embodiment of a microfluidic device in accordance with the present invention is generally designated by the reference numeral 60. Similar to microfluidic device 10, it is intended that microfluidic device 60 be affixed to the skin of individual 62. Microfluidic device 60 includes body 64 that defines reservoir 66 for receiving drug 68 therein. In addition, body 64 defines a pressure source cavity 70 for receiving a plurality of pressure sources 72, as hereinafter described. In addition, trigger 74 is positioned within the pressure source cavity 70 in body 64 of microfluidic device 60. Ports 76 and 78 are provided in body 64 to allow communication with reservoir 66 and pressure source cavity 70, respectively, with a syringe or the like.

Reservoir 66 and pressure source cavity 70 are separated by first flexible membrane 80. In addition, pressure source cavity 70 is isolated from input 82 of needle 84 by second flexible membrane 86. Second flexible membrane 86 is biased over input 82 to outlet needle 84 by trigger 74, as hereinafter described. Outlet needle 84 also includes output 88 that is receivable within the skin of an individual 62

Figure 7:
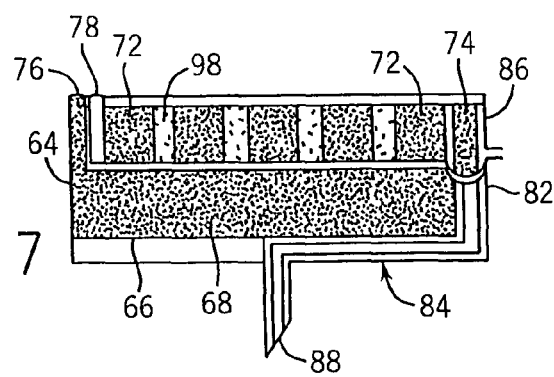
FIG. 7 is a schematic, cross-sectional view of the microfluidic device of FIG. 5 with the reservoir filled with a drug.
Figure 8:
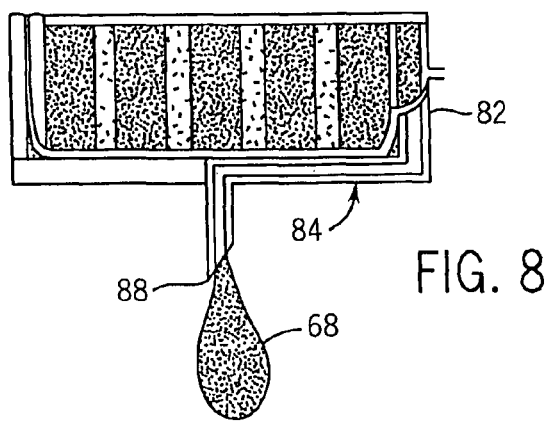
FIG. 8 is a schematic, cross-sectional view of the microfluidic device of FIG. 5 showing the drug being dispensed.

In operation, reservoir 66 is filed with drug 68 through port 76 in body 64. Thereafter, body 64 is positioned against the skin of individual 62 such that output 88 of outlet needle 84 communicates with the subcutaneous layer of the skin. In order to trigger operation of microfluidic device 60, buffer solution 98 is injected into pressure source cavity 70 through port 78 in body 64, FIG. 7. With buffer solution 98 within pressure source cavity 70, pressure sources 72 expand in response thereto. Simultaneously, trigger 74 begins to shrink. As trigger 74 shrinks, second flexible membrane 86 is withdrawn from input 82 of outlet needle 84 such that reservoir 66 is in communication with input 82 of outlet needle 84. As a result, as pressure sources 72 continue to expand, first flexible membrane 80 is urged into reservoir 66 causing drug 68 to flow from reservoir 66 into and through outlet needle 84, FIG. 8. Pressure sources 72 continue to expand at a constant rate over time such that drug 68 is dispensed into the subcutaneous layer of the skin of individual 62 at a constant rate over a predetermined time period.

It can be appreciated, that once drug 68 is expunged from reservoir 66, buffer solution 98 may be removed from pressure source cavity 70 so as to cause pressure sources 72 and trigger 74 to return to their original configuration. If another dosage of drug 66 is required, the process may be repeated.

Figure 9:
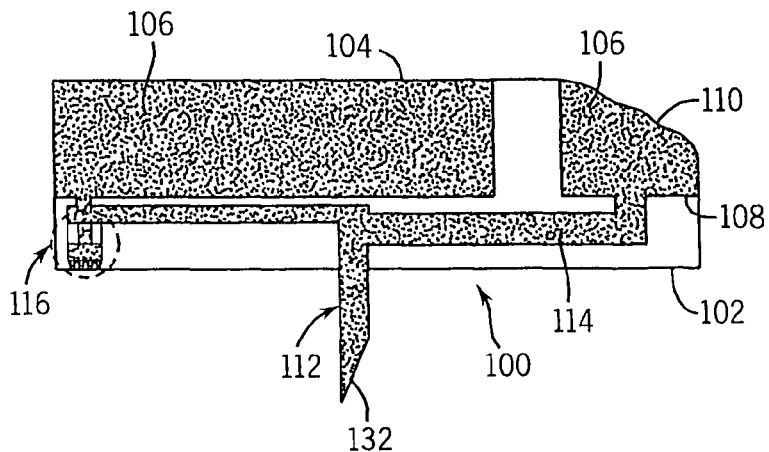
FIG. 9 is a third embodiment of a microfluidic device in accordance with the present invention.
Figure 10:
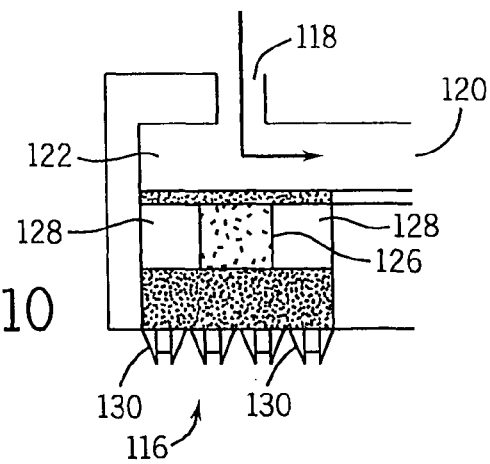
FIG. 10 is an enlarged, schematic view showing the valve of the microfluidic device of FIG. 9 in an open position.
Figure 11:
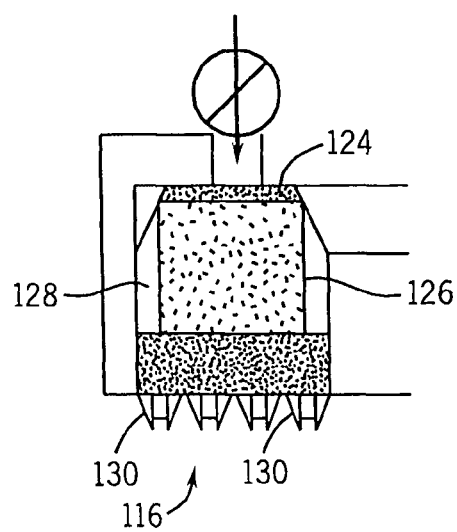
FIG. 11 is a schematic, cross-sectional view showing the valve of the microfluidic device of FIG. 9 in a closed position.

Referring to FIGS. 9-11, a still further embodiment of a microfluidic device in accordance with the present invention is generally designated by the reference numeral 100. Microfluidic device 100 includes body 102 defining first reservoir 104 for receiving drug 106 therein. In addition, body 102 defines second reservoir 108 for receiving a bolus of drug 106 therein. Flexible membrane 110 overlaps reservoir 108 and defines a bistable button, for reasons hereinafter described. Second reservoir 108 communicates with outlet needle 112 through flow conduit 114.

First reservoir 104 communicates with outlet needle 112 through valve 116. Valve 116 includes inlet 118 and outlet 120 that communicates with outlet needle 112. Valve 116 is movable between a closed position, FIG. 11, wherein the drug 106 is maintained within reservoir 104, FIG. 11, and an open position, FIG. 10 wherein drug 106 of reservoir 104 is free to flow through valve 116 into outlet needle 112.

Valve 116 includes drug flow chamber 122 disposed between input 118 and output 120 of valve 116 and trigger receiving chamber 128. Trigger receiving chamber 128 is isolated from drug flow chamber 122 by flexible membrane 124. Hydrogel trigger 126 is positioned within trigger receiving chamber 128 of valve 116. Hydrogel trigger 126 has a first enlarged configuration, FIG. 11, wherein hydrogel trigger 126 engages flexible membrane 124 and urges flexible membrane 124 against input 118 to valve 116 such that valve 116 is in its closed position, and a second retracted configuration, FIG. 10, wherein flexible membrane 124 is spaced from input 118 to valve 116 such that valve 116 is in its open position.

Valve 116 further includes a plurality of sensing needles 130 having inputs extending from body 102 of microfluidic device 100 and outputs in communication with trigger receiving chamber 128 of valve 116. It is intended that sensing needles 130 allow for the physiological fluids to pass from an individual into trigger receiving chamber 128 in valve 116.

In operation, valve 116 is initially in its closed position, FIG. 11, such that drug 106 is unable to flow from reservoir 104 to output needle 112. Body 102 of microfluidic device 106 is positioned against the skin of an individual such that outlet needle 112 is inserted into and communicates with the subcutaneous layer of the skin and such that sensing needles 130 allow physiological fluids to flow into trigger receiving chamber 128 of valve 116. In response to a predetermined condition of the physiological fluid flowing into trigger receiving chamber 128 of valve 116, hydrogel trigger 126 retracts from its expanded configuration, FIG. 11, to its retracted configuration, FIG. 10, thereby opening valve 116. With valve 116 open, drug 106 is free to flow through valve 116 and into outlet needle 112. As a result, drug 106 flows from outlet 132 of outlet needle 112 into the subcutaneous layer of skin of the individual. If the predetermined condition of the physiological fluid in trigger receiving chamber 128 of valve 116 is relieved, hydrogel trigger 126 returns to its expanded configuration, FIG. 11, so as to close valve 116.

With valve 116 in the closed position, drug 106 in reservoir 104 no longer flows through outlet needle 112 into the individual.

In such circumstances when a bolus of the drug 106 is immediately needed by the individual, it is contemplated to allow the individual to depress flexible membrane 110 thereby urging drug 106 from second reservoir 108 into flow conduit 114. Drug 106 flows through flow conduit 114 and outlet needle 112 into the subcutaneous layer of skin of the individual.

Figure 12:
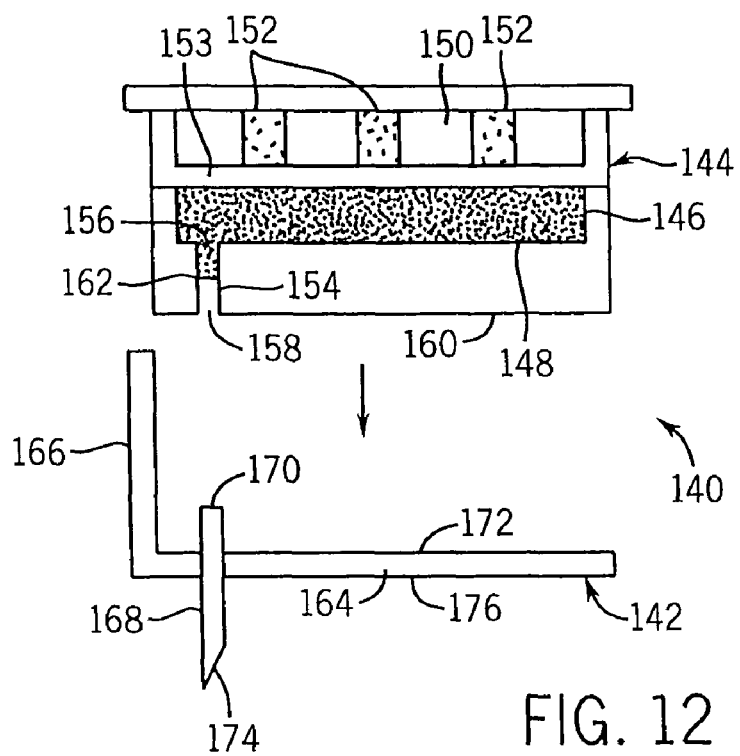
FIG. 12 is a schematic, cross-sectional view showing a fourth embodiment of the microfluidic device of the present invention.
Figure 13:
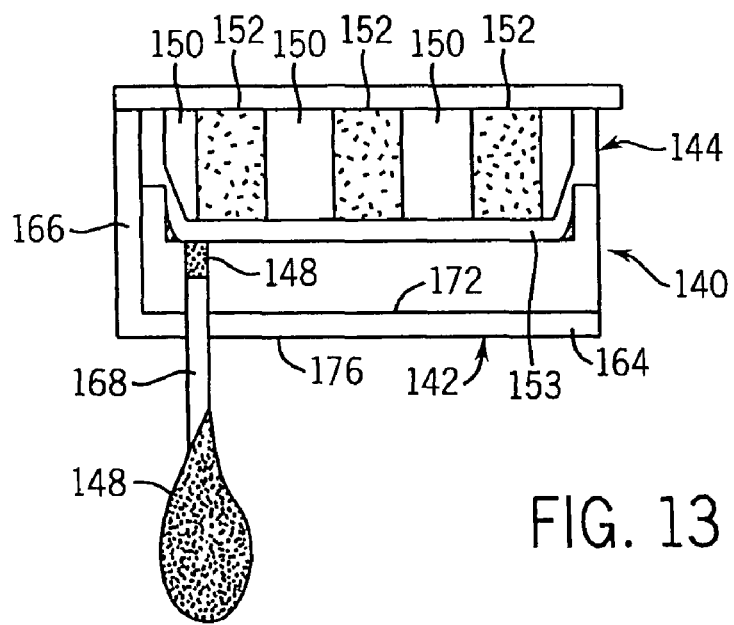
FIG. 13 is a schematic, cross-sectional view of the microfluidic device of FIG. 12 dispensing a drug.

Referring to FIGS. 12 and 13, a still further embodiment of the microfluidic device of the present invention is generally designated by the reference numeral 140. Microfluidic device 140 includes docking station 142 and body 144. Body 144 defines reservoir 146 for receiving drug 148 therein. In addition, body 144 includes pressure source chamber 150 for receiving a plurality of hydrogel pressure sources 152 therein. Hydrogel pressure sources 152 expand in response to exposure to a predetermined buffer solution. Body 144 further defines flow conduit 154 which includes inlet 156 communicating with reservoir 146 in body 144 and outlet 158 communicating with outer surface 160. Pierceable membrane 162 may be provided in flow conduit 154 to prevent the undesired flow of drug 148 from reservoir 146.

Docking station 142 includes base 164 extending along a first axis and an alignment support 166 extending normal thereto. Needle 168 extends through and is supported by base 164. Needle 168 includes inlet end 170 on first side 172 of base 164 and outlet end 174 on second side 176 of base 164. It is contemplated to provide an adhesive on second side 176 of base 164 for affixing docking station 142 to the skin of an individual.

In operation, body 144 is positioned against first side 172 of base 164 such that inlet end 170 of needle 168 extends into flow conduit 154 in body 144 through outlet end 158 thereof. It is intended that inlet end 170 of needle 168 of docking station 142 pierce membrane 162 within flow conduit 154 so as to allow drug 148 to flow into and through needle 168. Alignment wall 166 of docking station 142 facilitates the alignment of body 144 on first side 172 of base 164 of docking station 142.

With body 144 mounted on docking station 142, microfluidic device 140 is positioned against the skin of an individual such that needle 168 pierces the skin and outlet end 174 of needle 168 is in communication with the subcutaneous layer of the skin. Thereafter, a buffer solution is injected into pressure source chamber 150 within body 144 so as to cause hydrogel pressure sources 152 to expand. As hydrogel pressure sources 152 expand, flexible membrane 153 is urged into reservoir 146. As a result, drug 148 is forced from reservoir 146 through needle 168 into the subcutaneous layer of the skin of the individual. Once drug 148 has been dispensed from reservoir 146, body 144 may be removed from the docking station 142. Thereafter, a replacement body 144 having a full dosage of drug 148 in the reservoir 146 may be repositioned on docking station 142, as hereinafter described, and the process repeated. As described, needle 168 remains within the individual thereby reducing the frequency that the individual must insert a needle into his skin.

Various modes of carrying out the invention are contemplated as being within the scope of the following claims particularly pointing out and distinctly claiming the subject matter which is regarded as the invention.

We claim:

1. A microfluidic device for delivering a drug to an individual, comprising:
   a body defining a reservoir for receiving the drug;
   an output needle having an input in communication with the reservoir and an output receivable within the individual;
   an adhesive for affixing the body to the individual;
   a pressure source including an hydrogel member expandable in response to exposure to a predetermined physical property, the hydrogel member engageable with the reservoir and urging the drug from the reservoir through the output needle as the hydrogel member expands; and
   a valve defining a chamber and interconnecting the reservoir and the output needle, the valve movable between a non-actuated position wherein the valve prevents the flow of the drug from the reservoir to the output needle and an actuated position wherein the valve allows for the flow of the drug from the reservoir to the output needle, the valve including:
      a flexible membrane for dividing the valve chamber into a drug flow portion and a trigger receiving portion; and
      a trigger positioned within the trigger receiving portion of the valve chamber and having a first configuration with the valve in the non-actuated position and a second configuration with the valve in the actuated position; and
   a first sensing needle having an input receivable in the individual and an output within the trigger receiving portion of the valve chamber, the first sensing needle allowing physiological fluids to pass from the individual to the trigger receiving portion of the valve chamber.

2. The microfluidic device of claim 1 wherein the trigger includes a hydrogel post, the hydrogel post changing configuration in response to exposure to a predetermined condition in the physiological fluids.

* * * * *